United States Patent [19]

Stack et al.

[11] Patent Number: 5,235,055

[45] Date of Patent: Aug. 10, 1993

[54] ANTIPSYCHOTIC QUINOLINE DERIVATIVES OF BENZODIOXANMETHYLAMINE

[75] Inventors: Gary P. Stack, Ambler; Magid A. Abou-Gharbia, Glen Mills, both of Pa.

[73] Assignee: American Home Products Corporation, New York, N.Y.

[21] Appl. No.: 939,198

[22] Filed: Sep. 2, 1992

[51] Int. Cl.$^5$ ............... C07D 215/14; C07D 401/12; C07D 405/12

[52] U.S. Cl. .................................... 546/177

[58] Field of Search ........................... 546/177

[56] References Cited

U.S. PATENT DOCUMENTS 4,704,390  11/1987  Caprathe et al. ............... 546/177

FOREIGN PATENT DOCUMENTS

| | | | |
|---|---|---|---|
| 170213 | 2/1986 | European Pat. Off. | 546/16 |
| 236930 | 9/1987 | European Pat. Off. | 544/49 |
| 58-219114 | 12/1983 | Japan | 549/366 |
| 6407012 | 6/1964 | Netherlands | 549/366 |

OTHER PUBLICATIONS

Fozard, et al., Br. J. Pharmacol. 90, 273P (1987).
Chemical Abstracts, vol. 96 (11), Abst. No. 96:85434z, Mar. 15, 1982.

*Primary Examiner*—Alan L. Rotman
*Attorney, Agent, or Firm*—Richard K. Jackson

[57] ABSTRACT

A compound of the formula:

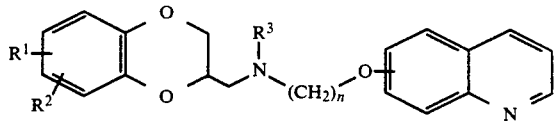

wherein $R^1$ and $R^2$ are, independently, hydrogen, alkyl, alkoxy, aralkoxy, alkanoyloxy, hydroxy, halo, amino, mono- or dialkylamino, alkanamido or sulfonamido, or $R^1$ and $R^2$ together are methylenedioxy, ethylenedioxy or propylenedioxy; $R^3$ is hydrogen or alkyl; n is one of the integers 2, 3 or 4; or a pharmaceutically acceptable salt thereof, are antipsychotic agents.

8 Claims, No Drawings

ANTIPSYCHOTIC QUINOLINE DERIVATIVES OF BENZODIOXANMETHYLAMINE

RELATED APPLICATION

Copending U.S. patent application Ser. No. 719,882, filed Jun. 21, 1991 discloses benzodioxin-2-ylmethylamino-alkoxy-quinolinone derivatives as antipsychotic agents.

BACKGROUND OF THE INVENTION

U.S. Pat. No. 4,704,390 claims compounds of the formula I as antipsychotic agents by virtue of their dopamine autoreceptor agonist activity. In formula I Het is selected from a group of heterocycles which includes the 2,3-pyrido, 3,4-pyrido and 2-hydroxy-3,4-pyrido moieties. X is carbon or nitrogen and A is phenyl or phenyl substituted by lower alkyl, lower alkoxy, lower thioalkoxy, halogen or trifluoromethyl, or A is 2-, 3- or 4-pyridinyl or 2-, 3- or 4-pyridinyl substituted by lower alkyl, lower alkoxy or halogen, or A is 2-, 4- or 5-pyrimidinyl or 2-, 4- or 5-pyrimidinyl substituted by lower alkyl, lower alkoxy or halogen, or A is 2-pyrazinyl or 2-pyrazinyl substituted by lower alkyl, lower alkoxy or halogen or A is 2- or 3-thienyl or 2- or 3-thienyl substituted by lower alkyl or hydrogen, or A is 2- or 3-furanyl or 2- or 3-furanyl substituted by lower alkyl or halogen, or A is 2- or 5-thiazolyl or 2- or 5-thiazolyl substituted by lower alkyl or halogen.

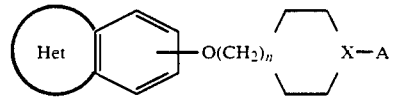

(I)

Jpn. Kokai Tokkyo Koho JP 57,142,972 and Fr. Demande FR 2,477,542 claim compounds of formula II as antihistaminic, anti-aggressive, and adrenaline antagonistic agents, useful as central nervous system agents. In this formula, R is H, alkyl, phenylalkyl, alkenyl, alkynyl; Z is N-phenylimino, (un)substituted benzylidene; n is 0 or 1; $Z^1$ is alkylene; and $Z^2$ is CO, CH(OH), (un)substituted vinylene or ethylene.

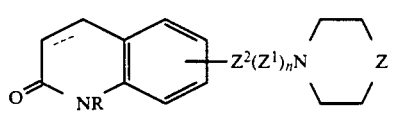

(II)

European Patent Application EP 170,213 discloses a series of N-alkylglutarimide derivatives of benzodioxan methanamine as antianxiety and antihypertensive agents.

Fozard et. al. Br. J. Pharmacol. 90, 273P (1987) disclose 8-[4-(1,4-benzodioxan-2-ylmethylamino)butyl]-8-azaspiro[4.5]decane-7,9-dione (MDL 72832) as a selective and stereospecific [(−)-MDL 72832 binds 32 times as much as the dextrorotary isomer at the 5-HT$_{1A}$ receptor site] ligand for 5-HT$_{1A}$ receptors.

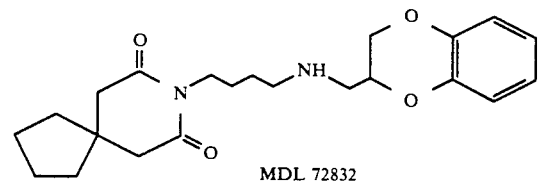

MDL 72832

European Patent EP 236,930 discloses a series of 2-substituted-alkyl-1,2-benzisothiazole-3-one 1,1-dioxide derivatives useful as anxiolytic and antihypertensive agents. Specifically claimed is 2-(4-(2,3-dihydro-1,4-benzodiox-2-yl)methylamino)butyl)-1,2-benzisothiazol-3(2H)-one 1,1-dioxide.

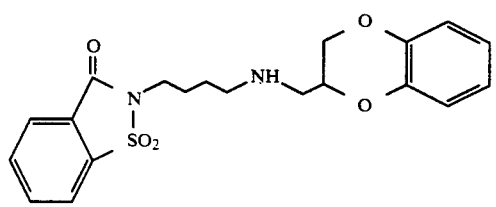

Netherlands 6,407,012 claims compounds of general formula III, in which R, R1 and R2 are H, halogen, (1–6C) alkyl, or (1–6C) alkoxy and n is an integer 2–6, as calming, hypnotic and hypotensive agents. Jpn. Kokai Tokkyo Koho JP 58,219,114 claims similar compounds in which $R_1$ and $R_2$ taken together represent methylenedioxy, ethylenedioxy or propylenedioxy ortho fused substituents on the phenoxy moiety.

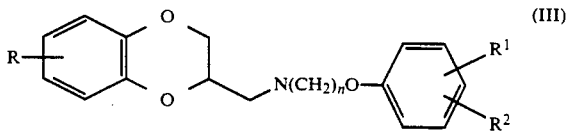

(III)

DESCRIPTION OF THE INVENTION

In accordance with this invention, there is provided a group of novel antipsychotic agents of the formula:

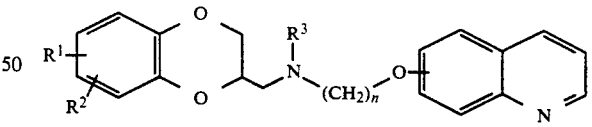

wherein
$R^1$ and $R^2$ are, independently, hydrogen, alkyl of 1–6 carbon atoms, alkoxy of 1–6 carbon atoms, aralkoxy of 7 to 12 carbon atoms, alkanoyloxy of 2 to 6 carbon atoms, hydroxy, halo, amino, mono- or dialkylamino in which each alkyl group has 1 to 6 carbon atoms, alkanamido of 2 to 6 carbon atoms, or sulfonamido, or $R^1$ and $R^2$ together are methylenedioxy, ethylenedioxy, or propylenedioxy;
$R^3$ is hydrogen or alkyl of 1 to 6 carbon atoms;
n is an integer 2,3 or 4;
or a pharmaceutically acceptable salt thereof.

Of these compounds, the preferred members are those in which $R^1$ and $R^2$ are, independently, fluoro, hydrogen, hydroxy, alkoxy of 1 to 6 carbon atoms or alkanoyloxy of 2 to 6 carbon atoms, or together form a methylenedioxy, ethylenedioxy or propylenedioxy ring; n and R³ are defined as above and the connection from the oxygen to the quinoline moiety is in the 7 position.

Most preferred are those members in which R¹ and R² are located in the 6 and 7 positions of the benzodioxan and are defined as fluoro, hydrogen, hydroxy, alkoxy of 1 to 6 carbon atoms or alkanoyloxy of 2 to 6 carbon atoms, or together form alkylenedioxy of 1 to 3 carbon atoms; R³ is hydrogen or alkyl of 1 to 6 carbon atoms, n is 3, the connection from the oxygen to the quinoline moiety is at C-7, and the stereochemistry of the benzodioxan methanamine is S.

The pharmaceutically acceptable salts are those derived from such organic and inorganic acids as: acetic, lactic, citric, tartaric, succinic, maleic, malonic, hydrochloric, hydrobromic, phosphoric, nitric, sulfuric, methanesulfonic, and similarly known acceptable acids.

The compounds of this invention are prepared by conventional methods. For example, the appropriately substituted benzodioxan methanamine is combined with a suitable alkyl halide in the presence of an acid scavenger such as diisopropylethylamine in a solvent such as dimethylformamide and heated at 80°-100° C. for 24 hours (1). Alternatively, a benzodioxan methylhalide or tosylate may be combined with the appropriate aminoalkoxyquinoline under similar conditions and heated for an extended period (2). The amine component may also be combined with a suitably substituted aldehyde and a reducing agent such as sodium cyanoborohydride (3), or with the appropriate acid chloride followed by reduction by an agent such as borane/THF (4).

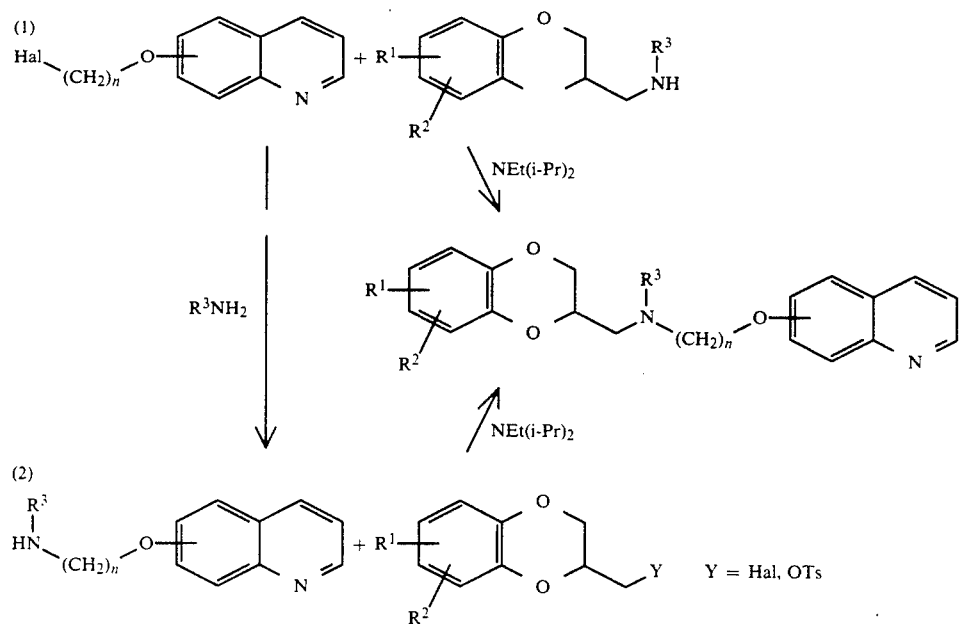

The haloalkoxyquinolines appropriate for the above procedure are known compounds; the aminoalkoxyquinolines may be readily prepared from them as shown above. The aldehydes and carboxylic acid chlorides appropriate to (3) and (4) may be readily prepared by one schooled in the art. The benzodioxan methanamines themselves are known compounds, or they can readily be derived from the appropriate salicylaldehyde by the procedure illustrated below. The benzodioxan methanamines may be resolved into their enantiomers by conventional methods or, preferably, they may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epichlorohydrin in the procedure below. Throughout this application, the name of a product of this invention, where the absolute configuration of the benzodioxan methanamine is not indicated, is intended to embrace the R and S isomers, as well as a mixture of the R and S isomers.

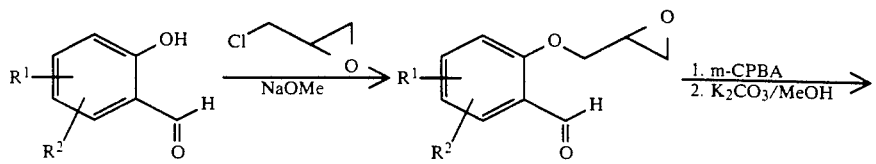

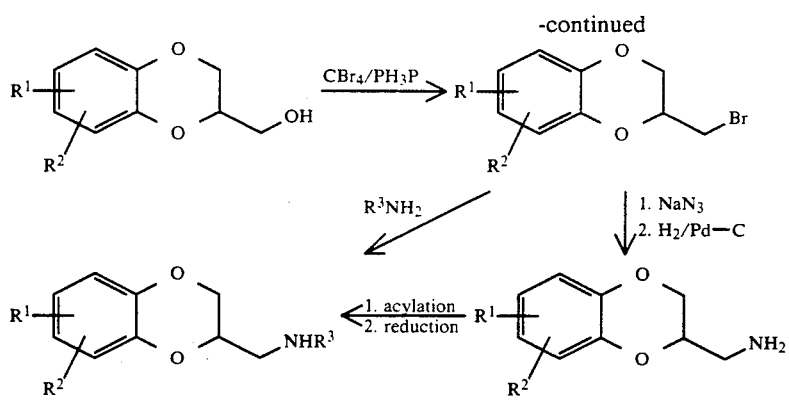

The compounds of this invention are dopamine autoreceptor agonists; that is, they serve to modulate the synthesis and release of the neurotransmitter dopamine. They are thus useful for treatment of disorders of the dopaminergic system, such as schizophrenia, Parkinson's disease and Tourette's syndrome. Such agents are partial agonists at the postsynaptic dopamine $D_2$ receptor and are thereby useful in the treatment of drug addiction.

The effect of the compounds of the invention on the synthesis of dopamine was established by the method of Walters and Roth, Naunyn-Schmiedeberg's Arch. Pharmacol. 296:5-14, 1976, in which rats (male, Sprague-Dawley, Charles River, 200-350 g) were administered vehicle or test drug ten minutes prior to the administration of gamma butyrolactone (GBL; 750 mg/kg, ip to inhibit dopaminergic impulse flow) and 20 minutes prior to NSD-1015 (100 mg/kg, ip to prevent the conversion of dopa to dopamine). Thirty minutes after NSD-1015 all rats were decapitated and the nucleus accumbens and the striatum were removed for analysis. Following perchloric acid extraction of the tissue, the extracts were placed over alumina columns to collect and concentrate dopa and other catechols. This eluate was then subjected to HPLC analysis using electrochemical detection to quantify the levels of dopa present. Dopamine autoreceptor agonists, under the conditions used above, inhibit dopa accumulation. The results of this testing with compounds representative of this invention are reported below as % inhibition of dopa accumulation at 10 mg/kg, sc in either limbic (L) or striatal (S) brain tissue.

The antipsychotic activity of the compounds of the invention was further established by a determination of the compounds' ability to reduce mouse locomotor activity according to the method of Martin and Bendensky, J. Pharmacol. Exp. Therap. 229:706-711, 1984, in which mice (male, CF-1, Charles River, 20-30 g) were injected with vehicle or various doses of each drug and locomotor activity was measured for 30 minutes using automated infrared activity monitors (Omnitech—8×8 inch open field) located in a darkened room. $ED_{50}$'s were calculated from the horizontal activity counts collected from 10 to 20 minutes after dosing using a nonlinear regression analysis with inverse prediction. The results of this test with compounds of the invention are reported below.

Affinity for the dopamine $D_2$ receptor was established by a modification of the standard experimental test procedure of Seemen and Schaus, European Journal of Pharmacology 203: 105-109, 1991, wherein homogenized rat striatal brain tissue is incubated with $^3$H-quinpirole and various concentrations of test compound, filtered and washed and counted in a Betaplate scintillation counter. The results of this testing with compounds representative of this invention are also given below.

The results of the standard experimental test procedures described in the preceding three paragraphs when applied to representative compounds of this invention were as follows:

| Compound | Dopa Accumulation (% inhib. @ 10 mg/kg, sc) | Hypolocomotion ($ED_{50}$ mg/kg, ip) | $D_2$ Receptor Affinity ($IC_{50}$(nM) or % @ ()μM) |
|---|---|---|---|
| Example 1 | 29 (L)/44 (S) | | |
| Example 2 | 60.4 (L) | 3.0 | 63 nM |
| Example 3 | 42.6 (L) | 12.6 | 25% (0.1) |
| Example 4 | | | 55% (0.1) |

Hence, the compounds of this invention have a pronounced effect on the synthesis of the neurotransmitter dopamine and thus are useful in the treatment of dopaminergic disorders such as schizophrenia, Parkinson's disease, Tourette's syndrome and drug addiction.

Applicable solid carriers for pharmaceutical compositions containing the compounds of this invention can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis and the size, age and response pattern of the patient.

The following examples illustrate the production of representative compounds of this invention.

EXAMPLE 1

N-[3-(Quinolin-7-yloxy)propyl]-2,3-dihydro-1,4-benzodioxin-2-methanamine 2,3-Dihydro-1,4-benzodioxin-2-methanamine (0.66 g, 4.0 mmole), 7-(3-bromopropoxy)quinoline (1.0 g, 3.8 mmole), and triethylamine (0.8 ml, 5.8 mmole) were combined in 50 ml of dimethylformamide and heated at 68° C. for 48 hours under a nitrogen atmosphere. The solvent was then removed and replaced with 100 ml of dichloromethane, whereupon a precipitate (0.72 g) formed which was shown by NMR to be unreacted bromopropoxyquinoline. The mother liquor was evaporated in vacuum to give 0.45 g of residue, which when treated with ethanolic HCl in ether yielded 0.3 g of the title compound as the dihydrochloride, monohydrate (m.p. 199°–201° C.).

Elemental Analysis for: $C_{21}H_{22}N_2O_3.2HCl. H_2O$ Calcd: C, 57.15; H, 5.94; N, 6.35. Found: C, 56.83; H, 5.73; N, 6.05.

EXAMPLE 2

N-[3-(Quinolin-7-yloxy)propyl]-2,3-dihydro-6,7-methylenedioxy-1,4-benzodioxin-2-methanamine 2,3-Dihydro-6,7-methylenedioxy-1,4-benzodioxin-2-methanamine (1.3 g, 6.2 mmole), 7-(3-bromopropoxy)quinoline (1.53 g, 5.5 mmole), diisopropylethylamine 2.6 g, 20 mmole) and sodium iodide (5.5 g, 37 mmole) were combined in 200 ml of DMF and heated at 80° C. for 15 hours under a nitrogen atmosphere. The solvent was then removed in vacuum and replaced with 500 ml of dichloromethane. The mixture was washed with 250 ml each of saturated aqueous sodium bicarbonate and saturated aqueous sodium chloride, dried over sodium sulfate, filtered, and concentrated in vacuum. The residue was column chromatographed on 250 g of silica gel using 3% methanol/dichloromethane as eluant. The product-containing fractions were combined and concentrated in vacuum and the residue (2.25 g) recrystallized from ethanol with the addition of 6 ml of 4N isopropanolic HCl to give 1.25 g of the title compound as a yellow solid dihydrochloride salt, m.p. 224°–226° C.

Elemental Analysis for: $C_{22}H_{22}N_2O_5.2$ HCl Calcd: C, 56.54; H, 5.18; N, 5.99 Found: C, 56.35; H, 5.23; N, 5.70

EXAMPLE 3

N-[3-(Quinolin-5-yloxy)propyl]-2,3-dihydro-6,7-methylenedioxy-1,4-benzodioxin-2-methanamine 2,3-Dihydro-6,7-methylenedioxy-1,4-benzodioxin-2-methanamine (2.3 g, 11 mmole), 5-(3-bromopropoxy)quinoline (2.54 g, 9.2 mmole), and diisopropylethylamine (2.6 g, 20 mmole) were combined in 100 ml of DMF and heated at 80° C. for 24 hours under a nitrogen atmosphere. The solvent was then removed in vacuum and replaced with 500 ml of dichloromethane. The mixture was washed with 250 ml each of saturated aqueous sodium bicarbonate and saturated aqueous sodium chloride, dried over sodium sulfate, filtered, and concentrated in vacuum. The residue was column chromatographed on 250 g of silica gel using 2% methanol/dichloromethane as eluant. The product-containing fractions were combined and concentrated in vacuum and the residue (2.0 g) recrystallized from 50 ml of ethanol with the addition of 6 ml of 4N isopropanolic HCl to give 1.4 g of the title compound as an orange solid dihydrochloride, one-quarter hydrate, m.p. 140°–145° C.

Elemental Analysis for: $C_{22}H_{22}N_2O_5.$ 2 HCl.$\frac{1}{4}$ $H_2O$ Calcd: C, 56.00; H, 5.23; N, 5.94 Found: C, 55.99; H, 5.59; N, 5.61

EXAMPLE 4

N-[3-(Quinolin-7-yloxy)propyl]-2,3-dihydro-7-methoxy-1,4-benzodioxin-2-methanamine 2,3-Dihydro-7-methoxy-1,4-benzodioxin-2-methanamine (2.7 g, 14 mmole), 7-(3-bromopropoxy)quinoline (3.86 g, 14 mmole), and diisopropylethylamine (6.5 g, 50 mmole) were combined in 100 ml of DMF and heated at 80° C. for 24 hours under a nitrogen atmosphere. The solvent was then removed in vacuum and replaced with 500 ml of dichloromethane. The mixture was washed with 250 ml each of saturated aqueous sodium bicarbonate and saturated aqueous sodium chloride, dried over sodium sulfate, filtered, and concentrated in vacuum. The residue was column chromatographed on 200 g of silica gel using 4% methanolchloroform as eluant. The product-containing fractions were combined and concentrated in vacuum and the residue recrystallized from 50 ml of ethanol with the addition of 8 ml of 4N isopropanolic HCl to give 1.5 g of the title compound as a yellow solid dihydrochloride monohydrate, m.p. 135°–142° C.

Elemental Analysis for: $C_{22}H_{24}N_2O_4.$ 2 $HCl.H_2O$ Calcd: C, 56.06; H, 5.99; N, 5.94 Found: C, 56.01; H, 5.99; N, 5.90.

EXAMPLE 5

N-[3-(Quinolin-7-yloxy)propyl]-2,3-dihydro-7-hydroxy-1,4-benzodioxin-2-methanamine N-[3-(Quinolin-7-yloxy)propyl]-2,3-dihydro-7-methoxy-1,4-benzodioxin-2-methanamine dihydrochloride monohydrate (0.94 g, 2.0 mmole), prepared above in Example 4, was dissolved in 10 ml of 48% HBr and refluxed for 24 hours under a nitrogen atmosphere. Upon cooling, the mixture was poured into 100 ml of saturated sodium bicarbonate solution to which 50 g of ice had been added. When the ice had melted, the mixture was extracted three times with 150 ml portions of 3:1 dichloromethane-isopropanol, the extracts dried over sodium sulfate, filtered, and concentrated in vacuum. The residue was column chromatographed on 50 g of silica gel with 3% methanol/chloroform and the product-containing fractions were combined and concentrated in vacuum. The crude free base thus obtained was crystallized from 50 ml of ethanol with the addition of 3 ml of 4N isopropanolic HCl to give 0.5 g of the title compound as a yellow dihydrochloride monohydrate, m.p. 245°-246° C.

Elemental Analysis for: $C_{21}H_{22}N_2O_4 \cdot 2\ HCl \cdot H_2O$
Calcd: C, 55.14; H, 5.73; N, 6.13 Found: C, 55.12; H, 5.65; N, 5.99

What is claimed is:

1. A compound of the formula:

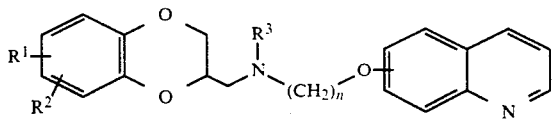

wherein $R^1$ and $R^2$ are, independently, hydrogen, alkyl of 1–6 carbon atoms, alkoxy of 1–6 carbon atoms, alkanoyloxy of 2 to 6 carbon atoms, hydroxy, halo, amino, mono- or dialkylamino in which each alkyl group has 1 to 6 carbon atoms, alkanamido of 2 to 6 carbon atoms, or sulfonamido, or $R^1$ and $R^2$ together are methylenedioxy, ethylenedioxy, or propylenedioxy;

$R^3$ is hydrogen or alkyl of 1 to 6 carbon atoms;

n is an integer 2, 3 or 4;

or a pharmaceutically acceptable salt thereof.

2. A compound of claim 1 in which $R^1$ and $R^2$ are, independently, fluoro, hydrogen, hydroxy, alkoxy of 1 to 6 carbon atoms or alkanoyloxy of 2 to 6 carbon atoms, or, taken together, $R^1$ and $R^2$ are methylenedioxy, ethylenedioxy or propylenedioxy and the $-(CH_2)_n-O-$ link is to the 7 position of the quinoline nucleus, or a pharmaceutically acceptable salt thereof.

3. A compound of claim 1 of the formula:

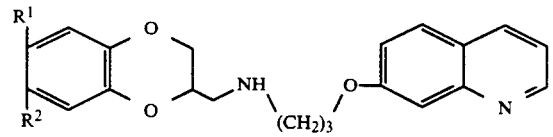

in which $R^1$ and $R^2$ are, independently, fluoro, hydrogen, hydroxy, alkoxy of 1 to 6 carbon atoms, alkanoyloxy of 2 to 6 carbon atoms, or, taken together, $R^1$ and $R^2$ are methylenedioxy, ethylenedioxy or propylenedioxy, or a pharmaceutically acceptable salt thereof, wherein the benzodioxan methanamine moiety is in the S-configuration.

4. The compound of claim 1 which is N-[3-(quinolin-7-yloxy)propyl]-2,3-dihydro-1,4-benzodioxin-2-methanamine, or a pharmaceutically acceptable salt thereof.

5. The compound of claim 1 which is N-[3-(quinolin-7-yloxy)propyl]-2,3-dihydro-6,7-methylenedioxy-1,4-benzodioxin-2-methanamine, or a pharmaceutically acceptable salt thereof.

6. The compound of claim 1 which is N-[3-(quinolin-5-yloxy)propyl]-2,3-dihydro-6,7-methylenedioxy-1,4-benzodioxin-2-methanamine, or a pharmaceutically acceptable salt thereof.

7. The compound of claim 1 which is N-[3-(quinolin-7-yloxy)propyl]-2,3-dihydro-7-methoxy-1,4-benzodioxin-2-methanamine, or a pharmaceutically acceptable salt thereof.

8. The compound of claim 1 which is N-[3-(quinolin-7-yloxy)propyl]-2,3-dihydro-7-hydroxy-1,4-benzodioxin-2-methanamine, or a pharmaceutically acceptable salt thereof.

* * * * *